US009920447B2

(12) United States Patent
Kurtz et al.

(10) Patent No.: US 9,920,447 B2
(45) Date of Patent: Mar. 20, 2018

(54) GRAPHENE ANTI-CORROSION COATING AND METHOD OF APPLICATION THEREOF

(71) Applicant: Luminit LLC, Torrance, CA (US)

(72) Inventors: Russell Kurtz, Palos Verdes Estates, CA (US); Mark Bennahmias, Ladera Ranch, CA (US)

(73) Assignee: LUMINIT LLC, Torrance, CA (US)

( * ) Notice: Subject to any disclaimer, the term of this patent is extended or adjusted under 35 U.S.C. 154(b) by 161 days.

(21) Appl. No.: 14/831,552

(22) Filed: Aug. 20, 2015

(65) Prior Publication Data
US 2016/0053398 A1   Feb. 25, 2016

Related U.S. Application Data

(60) Provisional application No. 62/040,826, filed on Aug. 22, 2014.

(51) Int. Cl.
*C25D 13/02* (2006.01)
*C01B 31/04* (2006.01)
*C09D 5/08* (2006.01)
*C25D 17/06* (2006.01)
*C25D 17/02* (2006.01)
*C25D 9/08* (2006.01)
*C25D 13/22* (2006.01)
*G01N 21/65* (2006.01)
*G01N 21/84* (2006.01)

(52) U.S. Cl.
CPC .......... *C25D 13/02* (2013.01); *C01B 31/0438* (2013.01); *C09D 5/084* (2013.01); *C25D 9/08* (2013.01); *C25D 13/22* (2013.01); *G01N 21/65* (2013.01); *G01N 2021/8411* (2013.01); *G01N 2021/8427* (2013.01)

(58) Field of Classification Search
CPC .... C01B 31/0438; C25D 15/00; C25D 15/02; C25D 17/16; C25D 17/26; C25D 17/00; C25D 13/02; C25D 13/14; C25D 13/12; C25D 13/22; G01N 2021/8411; G01N 2021/8427; G01N 21/65; B65G 49/00; B65G 49/0413; B65G 49/0418
See application file for complete search history.

(56) References Cited

U.S. PATENT DOCUMENTS

| | | | | |
|---|---|---|---|---|
| 5,128,006 A | * | 7/1992 | Mitchell | C25D 13/02 204/490 |
| 2009/0242921 A1 | * | 10/2009 | Aliyev | C25D 7/00 257/98 |
| 2016/0017502 A1 | * | 1/2016 | Santhanam | C25B 1/00 205/555 |

OTHER PUBLICATIONS

Wu et al., Adv. Mater., 2009, 21, 1756-1760.*
Singh et al., Carbon, 2013, 61, 47-56.*
Bykov et al., Physical Review B, 2012, 121413.*

* cited by examiner

*Primary Examiner* — Gurpreet Kaur
(74) *Attorney, Agent, or Firm* — Husch Blackwell LLP

(57) ABSTRACT

A graphene composite coating on a metal surface with excellent corrosion resistance by electrophoretic or electrolytic deposition has been obtained. The composite coating was shown to significantly increase the resistance of the metal surface to electrochemical degradation.

The graphene coating significantly reduces cathodic current, which is an indicator of the rate of corrosion at the interface between the cathodic material and the anodic material.

4 Claims, 4 Drawing Sheets

GRAPHENE ANTI-CORROSION COATING AND METHOD OF APPLICATION THEREOF

FIELD OF THE INVENTION

This invention relates to coatings, and more specifically to anti-corrosion coating.

BACKGROUND OF THE INVENTION

An innovative anti-corrosion surface coating to limit or control cathodic current density on structural materials like fasteners, pins, attachment points, and interfaces, commonly constructed from materials like copper-beryllium, CRES (corrosion resistant stainless steel), or titanium, without affecting the mechanical properties or function of the fastener substrate would be beneficial to society.

Additionally, maritime environments promotes corrosion of ship materials due to a high salt concentration (mainly sodium chloride), high electrical conductivity (4.8 Siemens/meter), relatively high and constant pH (7.5 to 8.4), and solubility for gases, of which oxygen and carbon dioxide particularly of high importance in the context of corrosion. The total annual impact cost of corrosion to U.S. shipping industry is currently estimated at $2.7 billion divided between new construction ($1.1 billion), maintenance and repairs ($0.8 billion), and corrosion-related downtime ($0.8 billion).

Recent active research of nanocomposite coatings, hydrophobic coatings and organic-inorganic hybrids have been shown to increase the life of materials prone to oxidation/corrosion. Such cutting edge coatings technologies have the market potential for a wide range of applications such as marine, pipeline, aerospace, automobiles and construction industries.

The discovery of graphene, a two dimensional, one atom thick, $sp^2$ hybridized carbon nanostructure—with its unique characteristics such as chemical inertness, electron transport, thermal and chemical stability, mechanical strength (breaking strength 100× that of steel and stiffness~1 TPa), high surface area (2630 m$^2$/g), and impermeability to ion diffusion (even light ions like He), have shown it to be one of the strongest candidates for corrosion resistance and protective coatings on metal.

SUMMARY OF THE PRESENT INVENTION

The present invention, a corrosion-resistant surface treatment, an extension of electrophoretic deposition manufacturing processes which presently fabricates custom engineered nano- and micro-textured nickel, chrome, and silver surfaces, utilizes the extraordinary mechanical, optical, and chemical properties of uniformly overlapping micron size graphene flakes.

The process of the subject invention uses a single-layer uniform coating process wherein parts are loaded into a rotating carousel fully integrated as part of an electrophoretic deposition (EPD) cell and immersed into a well-disbursed electrolytic suspension of micron-sized graphene flakes (which may be exfoliated from a graphite electrode). The carousel electrode ensures excellent adhesion and monolayer coverage onto a wide variety of substrates providing reduced corrosion susceptibility while preserving mechanical stability. Coatings thus fabricated have excellent cathodic current density reduction properties, offer scratch resistance, and to some degree will be self-cleaning due to the unique chemical properties of the overlapping graphene platelets.

When an electrical connection is established between two dissimilar metals in a conductive environment, electrons will flow from the more negative (active) surface to the more positive (noble) surface. The electrons that flow to the noble metal drive it to more negative potentials (cathodic polarization). This current flow and polarization correspond to an electron surplus that reduces the rate at which the noble metal corrodes. Graphite is one of the more noble materials.

A preferred embodiment of the present invention produces a sufficient amount of graphene nano-flakes by means of an array of tanks employing electrochemical exfoliation using at least one graphite rod immersed in a mixture of water and a suitable ionic liquid (e.g. 0.5M $H_2SO_4$ solution). A dc potential bias is applied between the rod(s) and the carousel, resulting in exfoliation of graphene flakes from the graphite rod(s). The exfoliated flakes (~1 to 10 μm in size) are stirred to produce a well dispersed suspension of the graphene in solution. Several tanks within the electrochemical farm are filled with the graphene based suspension adding in an appropriate mixture of aqueous electrolyte. An electrophoretic deposition cell, integrated with a rotating carousel (FIG. 1), preloaded with the parts to be coated, are immersed into the solution. A dc potential bias is applied between the rotating carousel, which acts as the cathode, and the graphite electrode(s), which act as the anode, to complete the electrical circuit in the EPD cell. As the carousel rotates each part over time is uniformly coated. The rotation of the parts carousel helps to insure the graphene suspension is always well dispersed. In an alternative embodiment the carousel rotates 90° to the axis of rotation shown in FIG. 1, thereby resulting in a more uniform and complete coating. The thickness of the coating is controlled by the applied potential bias and the deposition time (~30 minutes per coating run). To preserve the quality in the coating process a coupon is inserted during each coating run to monitor the degree of coverage and film quality using a combination of an in-situ surface second harmonic generation (SSHG) metrology station and Raman spectroscopy.

A robust graphene reinforced composite coating with excellent corrosion resistance by aqueous cathodic electrophoretic deposition (EPD), one aspect of the present invention, is obtained. The optimum EPD conditions, a coating thickness of around 40 nm is obtained at 10 V and deposition time of 30 s. The composite coating significantly increases the resistance of the metal to electrochemical degradation. Tafel analysis, the standard method of studying corrosion reactions, confirms that the corrosion rate exhibited by the composite coating made up of overlapping graphene nano-patches was an order of magnitude lower than that of bare copper.

The slope from a Tafel plot can be used to calculate the rate at which any electrochemical process approaches equilibrium. In corrosion chemistry this is usually due to the rusting process, but it can also be due to the oxygen-hydroxide process approaching equilibrium if it starts with excess $OH^-$ or $O_2$, as might be the case in basic solutions or air saturated solutions. If the corrosion potential in a Tafel plot is substantially negative relative to the native oxygen-hydroxide process then the value of the Tafel slope at the equilibrium potential can be taken to be the rate of corrosion and can be used to judge the effectiveness of an anti-corrosion coating.

A robust graphene reinforced composite coating with excellent corrosion resistance by aqueous cathodic electrophoretic deposition (EPD) is known. In this case the optimum EPD conditions, a coating thickness of around 40 nm was obtained at 10 V and deposition time of 30 s. The composite coating was shown to significantly increase the resistance of the metal to electrochemical degradation. Tafel analysis confirmed that the corrosion rate exhibited by the composite coating made up of overlapping Graphene nanoplatelets was an order of magnitude lower than that of bare copper.

When the overvoltage $\eta=E-E_e$ in an electrochemical reaction is small the exponential term of the current density at a potential E in terms of the exchange current density at any equilibrium potential, $E_e$, is given by $$I = I(0)\left\{\exp\left[-\frac{\alpha n F \eta}{RT}\right] - \exp\left[-\frac{(1-\alpha)nF\eta}{RT}\right]\right\}$$

where
  α is the transfer coefficient
  F is the Faraday constant=$9.6487 \times 10^4$ C mol$^{-1}$
  R is the molar constant=8.314 J K$^{-1}$ mol$^{-1}$
  T is the temperature
  n is the number of moles In the case where the overvoltage is sufficiently small then this equation can be expanded and all terms except the first two can be neglected so that the expression simplifies to a steady state relationship given by $$I=I(0)nF\eta/RT$$

In this regime the cathodic current will be inversely proportional to temperature and directly proportional to the overvoltage. However at the other end of the spectrum in the case of a large overvoltage to the cathodic reaction which is the condition with corrosion in maritime environments, only the first exponential term in the equation above is significant, the second term being very small by comparison. Hence the dependence of net cathodic current on the overvoltage results in $$\ln I = \ln I(0) - \alpha n F \eta / RT$$

or $$\eta = 2.303 RT \log I(0)/(\alpha n F) - 2.303 RT \log I/(\alpha n F)$$

arriving at the empirical equation put forth by Tafel which is ideal for the study of corrosion chemistry and cathodic processes.

CONCISE DESCRIPTION OF THE DRAWINGS

Further features and advantages of the subject invention will become clear with the aid of the following description with reference to the accompanying drawings, in which FIG. 1 shows a schematic of a representation apparatus for deposition of a graphene coating according to the subject invention.

DETAILED DESCRIPTION OF THE INVENTION

Figure 1:
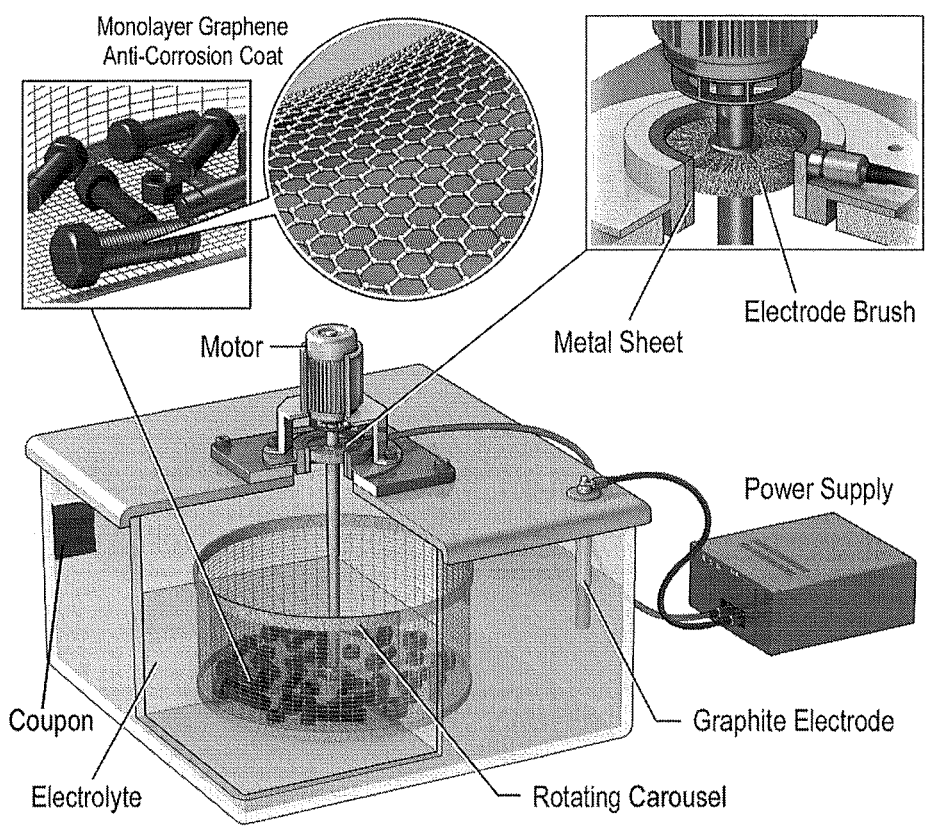

In this electroplating process the metal is the cathode and a graphite rod is the anode. Voltages tested so far were 5V and 10V. Electroplating times tested were 30 s and 60 s. Some coating procedures involved sonication, but the ones without sonication were still stirred at 400 rpm. For stainless steel, a hydrochloric acid bath was used to remove the anodic surface layer.

A number of electrolytes were used, with voltage between the cathode and anode tested at values from 5 V to 30 V, and with coating times between 5 s and 60 s. Some samples were also coated using a complete electrophoretic deposition (EPD) method, where both electrodes were Ti and the electrolyte contained a suspension of submicron graphene flakes. Standard half-cell potentials were used to estimate the voltage that would be needed for ELD. Using, for example, Ti in $K_2SO_4$ solution, it was determined that the minimum ionization level followed the equation

$$\text{Ti}(s) + 1.63 \text{ V} \rightarrow \text{Ti}^{2+},\qquad(0\text{-}1)$$

while the equivalent graphene reaction was ~1.04 V. Thus, the minimum Ti reaction would require 2.67 V, plus whatever is needed to move the graphene flakes and overcome entropy. Thus 5 V was selected as the minimum value for coating.

As stated above, the subject invention is a coating that significantly reduces cathodic current, which is an indicator of the rate of corrosion at the interface between the cathodic material (Ti, Cu, Fe) and an anodic material (usually Al). The coating system uses purely electrolytic deposition (ELD), in which a graphite anode provided the graphene flakes that were electrochemically bonded to the cathode (the materials used for the cathode were Ti 6/4, 316L CRES, and BeCu).

Each sample coated was a rod, 150 mm long×3 mm in diameter (7 mm² face area). One face of each rod was polished and that end of the rod was coated. The entire coated length of the rod, plus about 10 mm, was then covered with a piece of Teflon heat-shrink tubing and cured at 350° C. for up to 30 minutes, after which the excess of the tubing was cut off, almost exposing the coated face but leaving the uncoated end of the rod to attach to electricity. Rods of the coated metals were cut to 10 cm and then coated with graphene.

Tafel plots are slow scan linear voltammograms where the current is displayed as the logarithm of the current. If the graphene layer is effective in decreasing corrosion, then the corrosion potential, which is determined by the location of the dip in the Tafel plot, should move positive with the coating, which means that it is more difficult to start corrosion. The corrosion current, which is determined by the intersection of the linear fit of the cathodic and anodic currents, should decrease, meaning that corrosion is proceeding more slowly.

A first set of Tafel plots were taken of the graphene coated rods, then the rods were polished with 0.25 micron grit and then with 0.05 micron grit. They were then washed with deionized water, isopropanol, deionized water, and finally sonicated in millipore water for 10 min before a second set of Tafel plots for "uncoated" metal were taken.

Tafel analysis records current and voltage, compared to a standard Ag/AgCl electrode. This takes advantage of the empirical equation $$I = I_{ext} + I(V=0)\left\{\exp\left[-\frac{\alpha nFV}{RT}\right] - \exp\left[-\frac{(1-\alpha)nFV}{RT}\right]\right\}, \quad (0\text{-}2)$$

where V is the voltage at minimum current, α is a transfer coefficient, $F=9.6487\times10^4$ C/mol is the Faraday constant, $R=8.314$ J/K mol is the molar constant, T is the absolute temperature, and n is the number of moles. $I_{ext}$ is the current due to external reactions between the Ag/AgCl electrode and other chemicals in the electrolyte; the voltage related to this contributes to the voltage at which V=0.

The rods were tested in a solution of 3.5% NaCl in water. The water was not treated in any way to affect the oxygen content, so it is unlikely the water was oxygen-saturated, but it was definitely not deoxygenated. Direct measurement of corrosion current was also made.

Raman spectroscopy was performed with a Fisher Scientific Optical/Raman microscope in order to prove whether the rods were in fact coated with graphene. Coated rods were cut to 2 cm and held in place in a PVC block with a set screw so the smooth surface could be analyzed. Microphotographs were taken to select locations for the various Raman scans.

The spectra were taken with a 532 nm laser, 40× magnification, 5 mW power, and were corrected for fluorescence with a $6^{th}$ order polynomial. 48 scans were taken at 10 s per scan, with another 48 scans for background.

In the Raman scans, peaks near 1350 $cm^{-1}$, 1550 $cm^{-1}$, and possibly 2700 $cm^{-1}$ were observed in the scans of the coated rods but not in the scans of the uncoated rods.

Raman point spectra of the coated Ti rods showed peaks at 1350 $cm^{-1}$ and 1560 $cm^{-1}$ which were not present in the spectrum of uncoated Ti, and correspond to graphene.[14] This indicates that the Ti was definitely coated with graphene successfully.

Tafel plots of Ti coated with graphene oxide at 10 V, for 60 s, while sonicating, showed a reduction of corrosion current and increase of corrosion voltage that indicated they were essentially impervious to corrosion by rusting. As described above, the corrosion potential of the system is shown in a Tafel plot as the potential (horizontal coordinate) where the graph dips precipitously. The apparent corrosion potential for the coated rods is ~0.2V vs Ag/AgCl which is the same as the $O_2/OH^-$ redox couple, indicating that the $O_2/OH^-$ redox couple is the only one present and there is no actual corrosion of the metal or the graphene coating. Previous to treatment, the corrosion potential of the metal is ~-0.15V vs Ag/AgCl. An example of this analysis can be found in FIG. 2.

Figure 2:
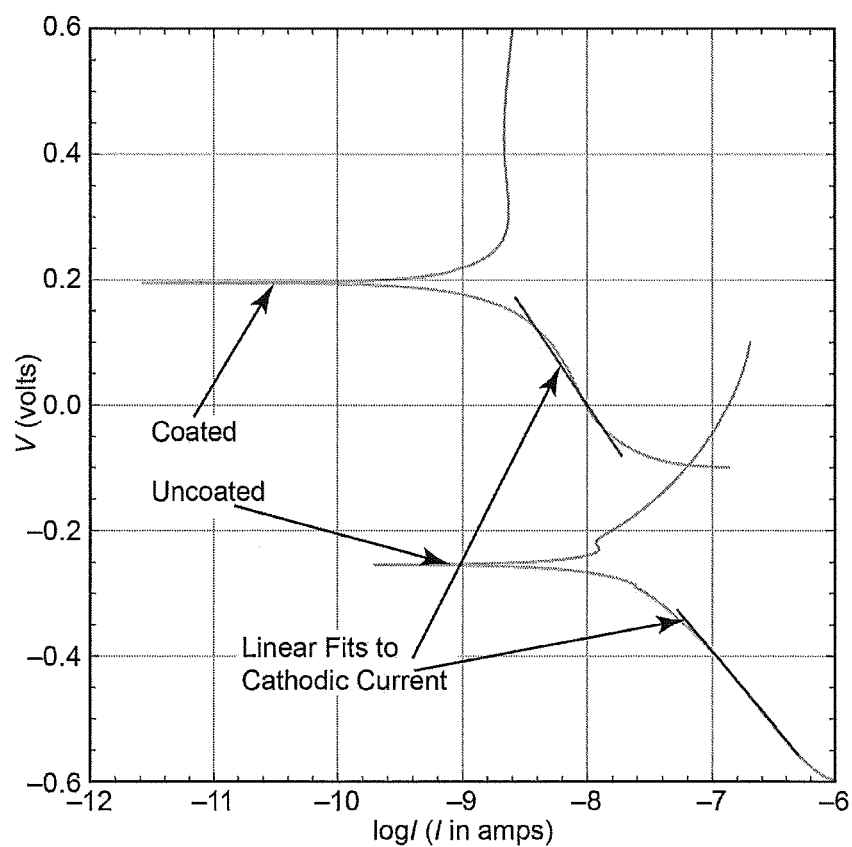
FIG. 2 is a Tafel plot of coated and uncoated Ti rods.

In FIG. 2 linear fits are included to show how corrosion currents are determined. With coating, the corrosion potential moves positive and the corrosion current decreases, thus showing that coating Ti with this method improves corrosion resistance, coating with sonication is best for Ti coating. This figure also shows the apparent corrosion current measurement by showing the linear fit of the cathodic and anodic currents in the Tafel plots of coated and uncoated Ti. The corrosion current is the current coordinate (vertical axis) where the lines meet on a Tafel plot and is the measure of the rate at which an electrochemical reaction such as rusting takes place. Here the apparent corrosion current from the Tafel plot of the coated Ti actually refers to both the rate at which the $O_2/OH^-$ reaction occurs and the rate of oxidation of this, not quite ideally coated sample.

Figure 3:
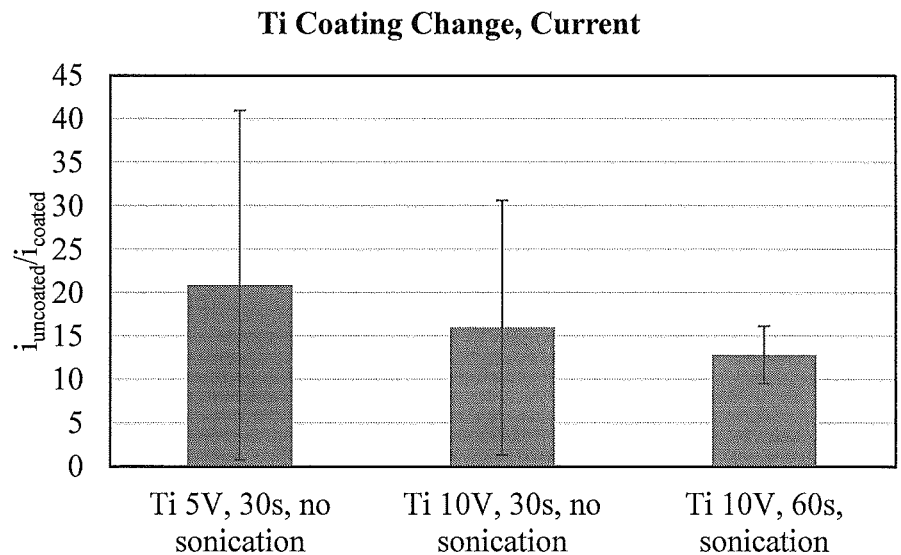
FIG. 3 is a graph showing the change in the corrosion potential of a coated Ti rod.
Figure 4:
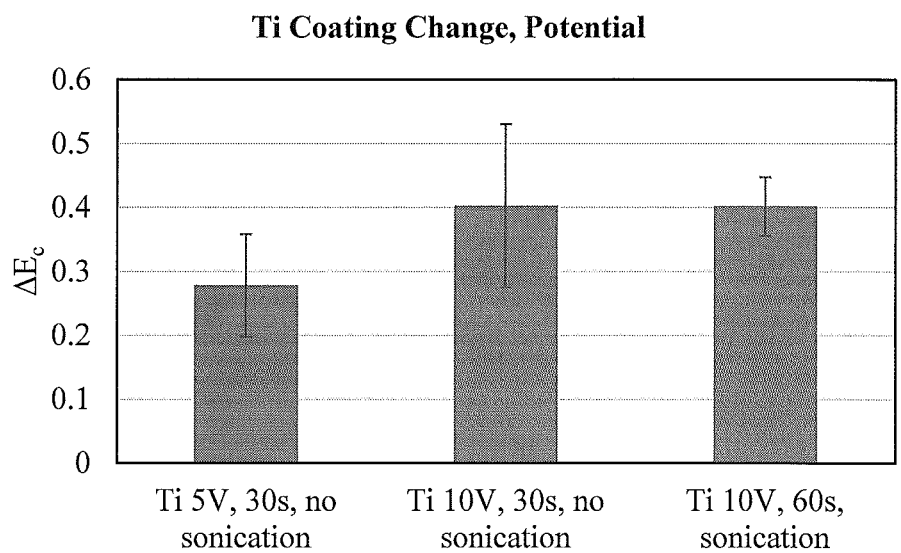
FIG. 4 is a graph showing the change in the corrosion current of a coated Ti rod.

Several coating methods were attempted and compared for the Ti samples. Comparing FIGS. 3 and 4, and it is seen that the method with the greatest voltage, time, and with sonication resulted in the greatest shift in corrosion potential which likely indicates that it is the most effective barrier.

Figure 5:
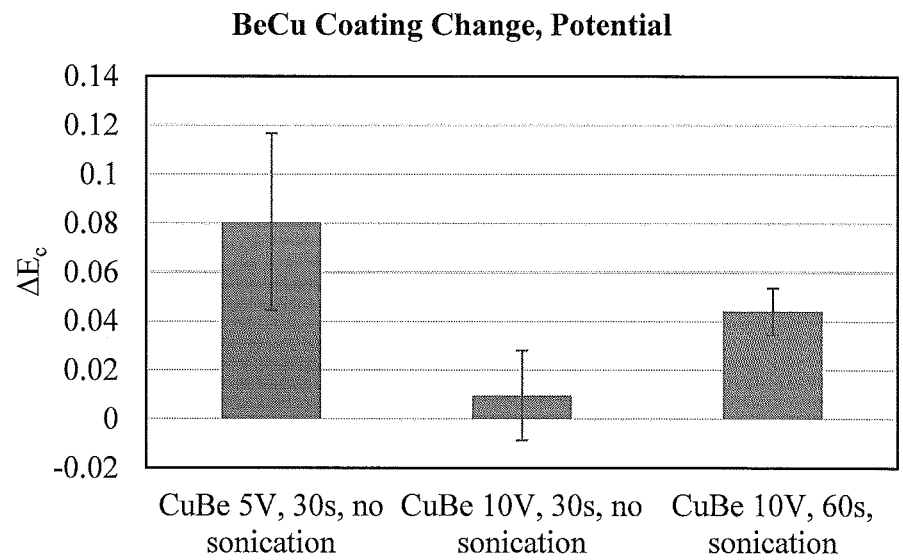
FIG. 5 is a graph showing the change in the corrosion potential of a coated BeCu rod.
Figure 6:
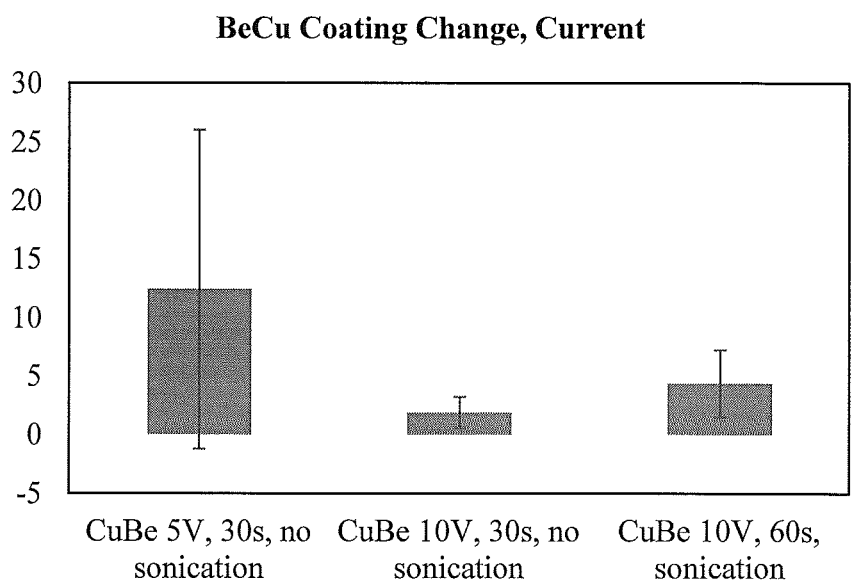
FIG. 6 is a graph showing the changes in the corrosion current of a coated BeCu rod.

FIGS. 5 and 6 are comparisons of different methods for coating BeCu. FIG. 5 shows graphene 5 V, 30 s, with no sonication, to be the most effective, but also the least reproducible.

The invention claimed is:

1. A method of coating a single layer of graphene flakes comprising the steps of:
   1) loading objects to be coated into a rotating carousel;
   2) immersing the rotating carousel into an electrolytic suspension of graphene flakes;
   3) locating a graphite rod outside the rotating carousel and within the electrolytic suspension;
   4) applying a dc potential bias between the rotating carousel and the graphite rod; and
   5) rotating the carousel;
thereby uniformly coating the objects on all surfaces with the graphene flakes.

2. The method of claim 1 further including the step of creating the electrolytic suspension of graphene flakes by exfoliating graphene flakes from the graphite rod.

3. The method of claim 1, further including the step of sonicating the coated object.

4. An electrophoretic deposition cell comprising:
   a power source,
   a tank,
   a rotating carousel within the tank including a porous basket for containing an object to be created,
   a graphite anode,
   an electrolytic suspension of graphene flakes in the tank and, the rotating carousel is a cathode,
   the graphite anode is outside the carousel, and
   a dc potential bias exists between the rotating carousel and the graphite electrode.

* * * * *